(12) United States Patent
Rome

(10) Patent No.: US 7,063,685 B2
(45) Date of Patent: Jun. 20, 2006

(54) HEMOSTASIS VALVE FOR A CATHETER

(75) Inventor: Guy Rome, West Valley City, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 10/844,276

(22) Filed: May 12, 2004

(65) Prior Publication Data

US 2005/0256457 A1   Nov. 17, 2005

(51) Int. Cl.
*A61M 5/00* (2006.01)
(52) U.S. Cl. .................. 604/256; 604/167.01
(58) Field of Classification Search .......... 604/167.06, 604/99.04, 122, 118, 119, 164.02, 167.02, 604/167.03, 167.04, 167.05, 186, 256, 236, 604/323, 237, 238, 247, 99.02, 99.03, 32, 604/33, 248, 249, 167.01; 251/149.2, 149.6
See application file for complete search history.

(56) References Cited

U.S. PATENT DOCUMENTS

| | | | | |
|---|---|---|---|---|
| 3,288,142 A | * | 11/1966 | Hakim ........................ 604/9 |
| 3,593,854 A | * | 7/1971 | Swank ...................... 210/326 |
| 3,868,973 A | * | 3/1975 | Bierman et al. ............. 138/43 |
| 4,000,739 A | | 1/1977 | Stevens |
| 4,233,982 A | * | 11/1980 | Bauer et al. ................ 604/256 |
| 4,245,635 A | * | 1/1981 | Kontos ................. 604/167.03 |
| 4,261,357 A | * | 4/1981 | Kontos ................. 604/167.01 |
| 4,379,458 A | * | 4/1983 | Bauer et al. ................ 604/264 |
| 4,387,879 A | | 6/1983 | Tauschinski |
| 4,424,833 A | | 1/1984 | Spector et al. |
| 4,430,081 A | | 2/1984 | Timmermans |
| 4,436,519 A | * | 3/1984 | O'Neill ...................... 604/175 |
| 4,473,067 A | | 9/1984 | Schiff |
| 4,534,759 A | * | 8/1985 | Trawoger ................... 604/117 |
| 4,610,665 A | | 9/1986 | Matsumoto et al. |
| 4,626,245 A | | 12/1986 | Weinstein |
| 4,650,472 A | | 3/1987 | Bates |
| 4,655,752 A | * | 4/1987 | Honkanen et al. .......... 604/256 |
| 4,673,393 A | | 6/1987 | Suzuki et al. |
| 4,917,668 A | * | 4/1990 | Haindl .................. 604/167.03 |
| 5,000,745 A | | 3/1991 | Guest et al. |
| 5,053,013 A | | 10/1991 | Ensminger et al. |
| 5,092,857 A | | 3/1992 | Fleischhacker |
| 5,108,380 A | * | 4/1992 | Herlitze et al. ............. 604/533 |
| 5,269,771 A | * | 12/1993 | Thomas et al. ............. 604/539 |
| 5,322,518 A | * | 6/1994 | Schneider et al. .......... 604/247 |
| 5,356,394 A | * | 10/1994 | Farley et al. ................ 604/256 |
| 5,358,490 A | | 10/1994 | Henry et al. |
| 5,643,227 A | | 7/1997 | Stevens |
| 5,743,883 A | * | 4/1998 | Visconti ................ 604/167.02 |
| 5,749,861 A | | 5/1998 | Guala et al. |
| 6,036,171 A | * | 3/2000 | Weinheimer et al. .... 251/149.1 |
| 6,089,539 A | * | 7/2000 | Kouda ..................... 251/149.2 |
| 6,482,188 B1 | | 11/2002 | Rogers et al. |
| 6,551,283 B1 | | 4/2003 | Guo et al. |

(Continued)

*Primary Examiner*—Nicholas Lucchesi
*Assistant Examiner*—Theodore J. Stigell
(74) *Attorney, Agent, or Firm*—Morrison & Foerster, LLP

(57) ABSTRACT

A hemostasis valve that is closed when not accessed, but which provides an unobstructed fluid pathway when accessed by a luer fitting/connector. An auto-closure valve within the hemostasis valve housing is flush with a top surface thereof, allowing easy cleaning (swabable) and maintenance when not accessed. When accessed with a connector or luer fitting, the valve opens completely, allowing an unobstructed high flow fluid path.

11 Claims, 3 Drawing Sheets

U.S. PATENT DOCUMENTS

| | | |
|---|---|---|
| 6,575,960 B1 | 6/2003 | Becker et al. |
| 2003/0098430 A1 | 5/2003 | Leinsing et al. |
| 2005/0113805 A1 | 5/2005 | Devellian et al. |
| 2005/0192537 A1 | 9/2005 | Osborne et al. |

* cited by examiner

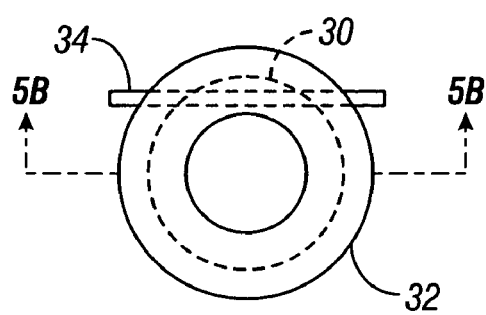
FIG. 5A
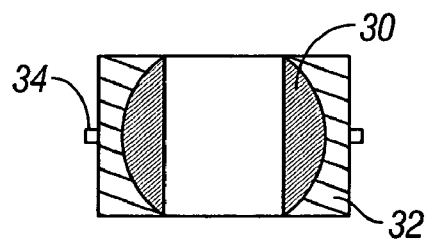
FIG. 5B
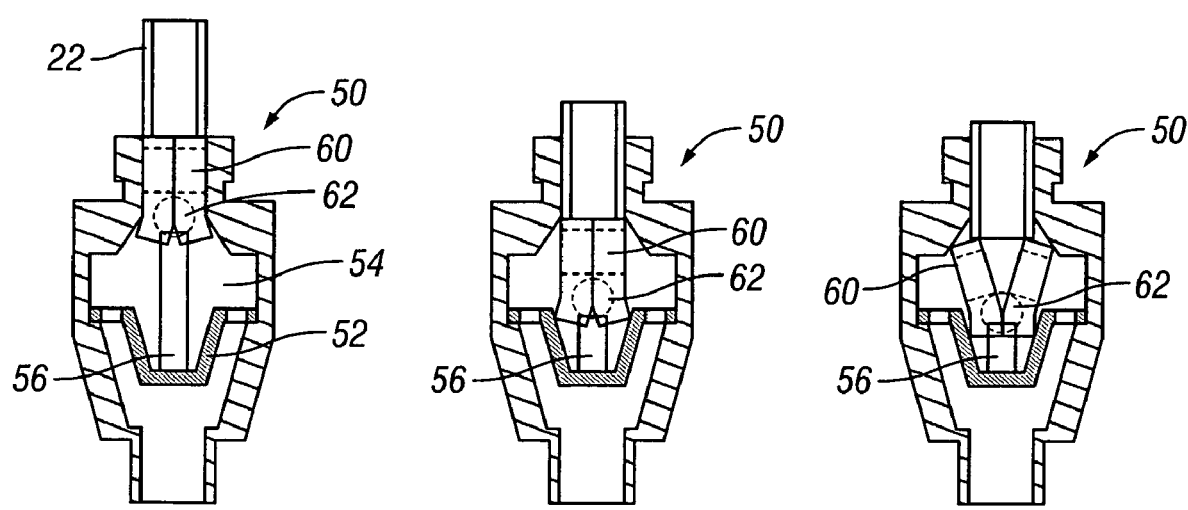
FIG. 6A          FIG. 6B          FIG. 6C

HEMOSTASIS VALVE FOR A CATHETER

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A COMPACT DISK APPENDIX

Not applicable.

FIELD OF INVENTION

The present invention is generally in the field of medical devices. More particularly, the present invention relates to a hemostasis valve connector intended for use with a catheter.

BACKGROUND OF THE INVENTION

There are a variety of conditions that require injection of fluids into, or withdrawing fluids from, parts of a body below the surface of the skin of the body. Thus, there are a wide variety of multi-lumen catheters available for such use. One aspect of vascular access with catheters involves insertion of the catheter into a blood vessel, which has risks associated therewith such as air embolism and blood loss. With respect to access of an arterial vessel, high pressures may result in the significant loss of blood without the use of a valve that closes the proximal end of the accessing instrument. In prior art systems, clamps or manual pinching of the accessing device have been used as methods to prevent blood loss. However, it would be advantageous in a catheter to offer a connector with a hemostasis valve that would permit vascular access without the associated risks of air embolism and blood loss.

Unfortunately, there are several problems with the currently offered valves for use with an open ended catheter. For example, the flow path through the valve may be restricted due to a restricted cross-sectional area, there exists a dead space above or below the valve where blood accumulates, making it difficult to clean the valve, and use of a guidewire traversing through the valve is often not enabled. In addition, many of the currently offered valves cannot be accessed multiple times as they are typically screwed on to a catheter and discarded after use.

Therefore, there is a need for a hemostasis valve that solves the above-mentioned problems and thereby reduces the risk of contamination and permits repeated use of the valve.

SUMMARY OF THE INVENTION

The hemostasis valve of the present invention includes one or more of the following characteristics: (a) accessible by a male luer fitting/connector, (b) sealed when not accessed, but provides an unobstructed fluid pathway when accessed with a male luer fitting/connector, (c) automatically closes if the male luer fitting/connector is disconnected to prevent blood loss or air embolism, (d) provides multiple access for a syringe or guidewire for an "over the guidewire" placement or replacement technique, (e) reduces the risk of infection by being sealed when not accessed, but exposes the closed end to the environment to be swabbed with an antiseptic prior to opening of the valve, and (f) is no larger than a luer fitting used in medical applications far delivery of fluid into the human body.

In one embodiment of the present invention, a hemostasis valve comprises a hemostasis valve housing having an inlet, an outlet, a cavity therebetween and a first guide slot, wherein said inlet is sized to receive a luer fitting; a ball valve housing; a ball valve positioned in said ball valve housing and having a second guide slot; a guide pin positioned in said first and second guide slots; and a biasing element supporting said ball valve housing, wherein said hemostasis valve is biased in a closed position, but which opens to permit substantially unobstructed fluid flow therethrough when accessed by said luer fitting.

In another embodiment of the present invention, a hemostasis valve comprises a hemostasis valve housing having an inlet, an outlet, a cavity therebetween and a first guide slot, wherein said inlet is sized to receive a luer fitting; a plug valve having two connected halves each comprising an angled bottom portion; and a biasing element supporting said plug valve, biasing said hemostasis valve in a closed position, wherein said angled bottom portion of each of said two connected halves is configured to engage a base of said hemostasis valve housing cavity to open said hemostasis valve for fluid flow therethrough.

These and other embodiments, features and advantages of the present invention will become more apparent to those skilled in the art when taken with reference to the following more detailed description of the invention in conjunction with the accompanying drawings that are first briefly described.

BRIEF DESCRIPTION OF THE DRAWINGS

In the accompanying drawings, reference characters refer to the same parts throughout the different views. The drawings are intended for illustrating some of the principles of providing a hemostasis valve. The drawings are not necessarily to scale, emphasis instead being placed upon illustrating the depicted principles in a clear manner.

FIGS. 5A–5B illustrate a top view and a sectional view of the ball valve of the present invention.

FIGS. 6A–6C illustrate a hemostasis valve incorporating a plug valve having a sliding cylinder that is angled at the bottom and shaped in two halves.

DETAILED DESCRIPTION OF THE INVENTION

Figure 1A:
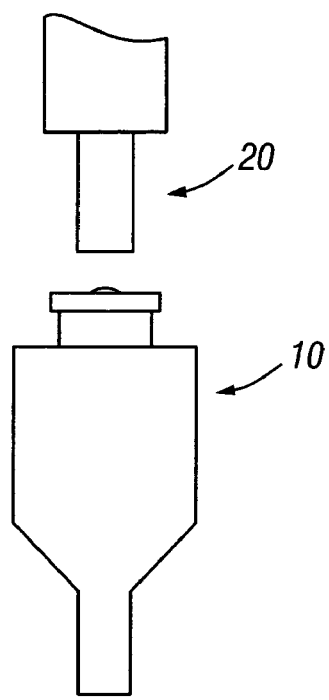
FIGS. 1A–1B illustrate a schematic of a hemostasis valve in the closed position.

The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

One embodiment is a hemostasis valve design that is closed when not accessed, but which provides an unobstructed fluid pathway when accessed by a luer fitting/connector. An auto-closure valve within the hemostasis valve housing is flush with a top surface thereof, allowing easy cleaning (swabable) and maintenance when not accessed. When accessed with a connector or luer fitting, the valve opens completely, allowing an unobstructed high flow fluid path. The valve assembly is small enough to fit into a modified luer connector housing (hemostasis valve housing) that is attachable to a catheter or catheter extension tubes.

An auto-closure valve, for example a ball valve, of the hemostasis valve is built-in the opening of the hemostasis valve and automatically seals the opening of the hemostasis valve except when being accessed by luer fitting, such as that of a syringe. One feature of the auto-closure valve is to seal off the open end of the hemostasis valve when the luer fitting is not attached, preventing blood loss or air embolism that may occur if the luer fitting is removed. On the other hand, the hemostasis valve provides unobstructed flow path without any pinched or reduced orifice in the opening of the hemostasis valve when the luer fitting is attached to the hemostasis valve. Because a straight fluid flow pathway is provided by the valve of the present invention, turbulence is reduced or eliminated. This design enables high flow without fluid restrictions, which is important, for example, for use with catheters having such requirements (e.g., dialysis catheters, power PICCs, etc.).

One design feature utilizes the hemostasis valve to be attached to an attachable device such as a syringe having a luer fitting. With a syringe attached to one end of the hemostasis valve and a catheter attached to the other end of the hemostasis valve, the catheter may be infused (flushed with saline) or aspirated. By utilizing the hemostasis valve in conjunction with a catheter, adapters and clamps are unnecessary as the design prevents blood loss or air embolism from occurring if a luer connected to the valve becomes detached therefrom. Another design feature of the hemostasis valve of the present invention is that the configuration provides for substantially zero dead space. One variation of the hemostasis valve allows passage of a standard guidewire or catheter through the valve opening. Yet other design feature of the hemostasis valve is that it can be accessed multiple times without the risk of being punctured or creating infection because the auto-closure valve can be swabbed with an antiseptic before opening the flow path of the hemostasis valve. Also, the hemostasis valve could be designed to be no larger than a standard luer fitting connector of a syringe, for example, and the valve could be located within the inside or outside the human body so long as the inlet of the hemostasis valve can be accessed by a luer fitting.

Figure 1B:
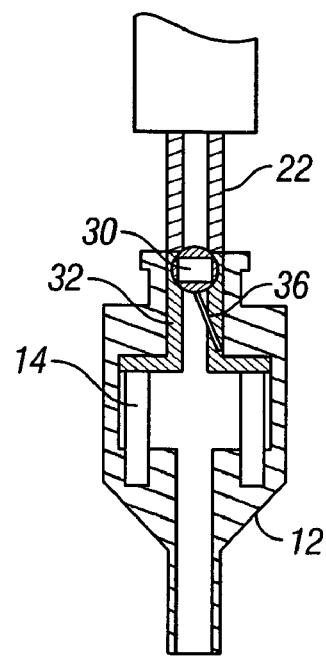

FIGS. 1A and 1B show a schematic of a hemostasis valve 10 in the closed position prior to access of a syringe 20. In particular, the hemostasis valve 10 is in a closed position with the opening trough a ball valve 30 being at about 90 degrees to the flow path through the hemostasis valve 10. FIG. 1A shows a side-view of the hemostasis valve with a luer fitting removed from the opening of the hemostasis valve. FIG. 1B shows a sectional view of the hemostasis valve 10 having a housing 12, with a luer fitting 22 of the syringe 20 just touching the ball valve housing 32 of the hemostasis valve 10 but without the ball valve housing 32 having been depressed by the mar fitting 22. The ball valve housing 32 is seated on a biasing element such as a spring 14 such that the ball valve housing 32 remains pressed to the inside roof of the cavity of the hemostasis valve 10. The ball valve 30 is seated within the ball valve housing 32 and is connected to the housing 12 via a guide pin 34 of the ball valve 30, which is positioned within a guide slot 36 of the housing 12 such that the ball valve 30 rotates about 90 degrees when the ball valve housing 32 is depressed from the roof to near the floor of the cavity of the hemostasis valve 10. The guide slot 36 is built-in as a slot preferably a linear slot within the hemostasis valve housing 12, preferably at an angle to the flow path near the luer fitting end of the hemostasis valve housing 12.

Figure 2:
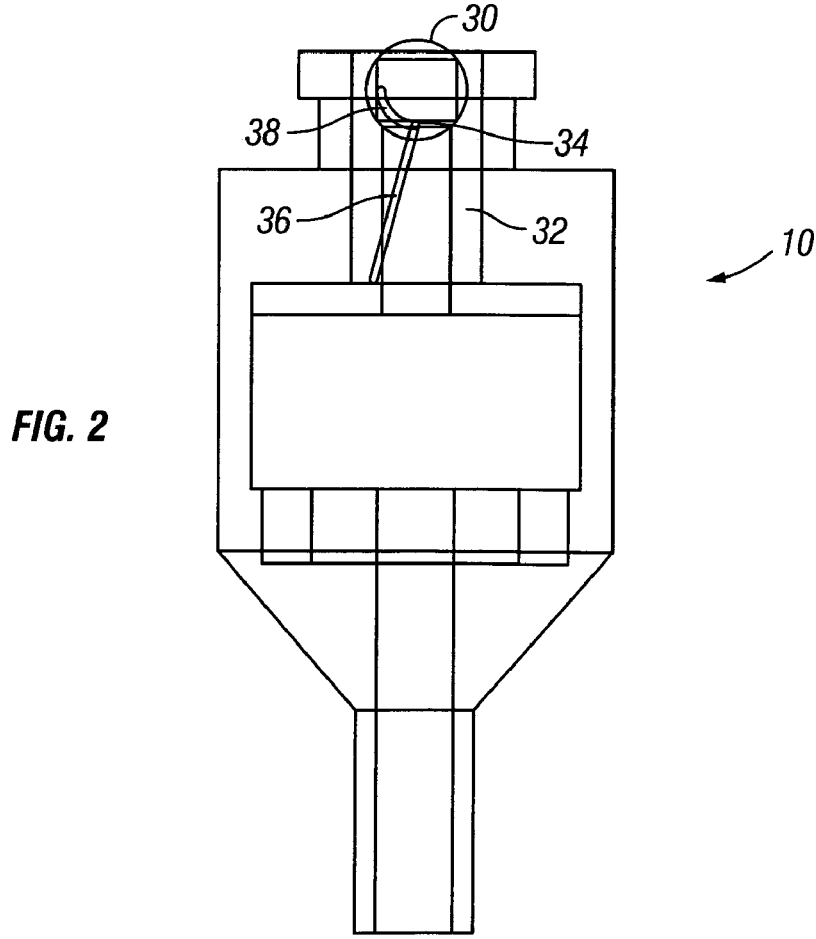
FIGS. 2–4 illustrate sectional views of the hemostasis valve with the ball valve housing positioned at the roof, the middle and the floor of the cavity of the hemostasis valve.
Figure 3:
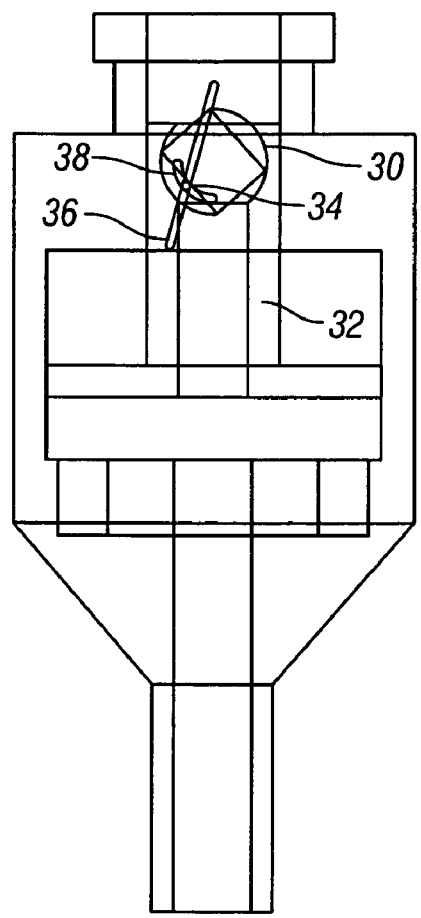
Figure 4:
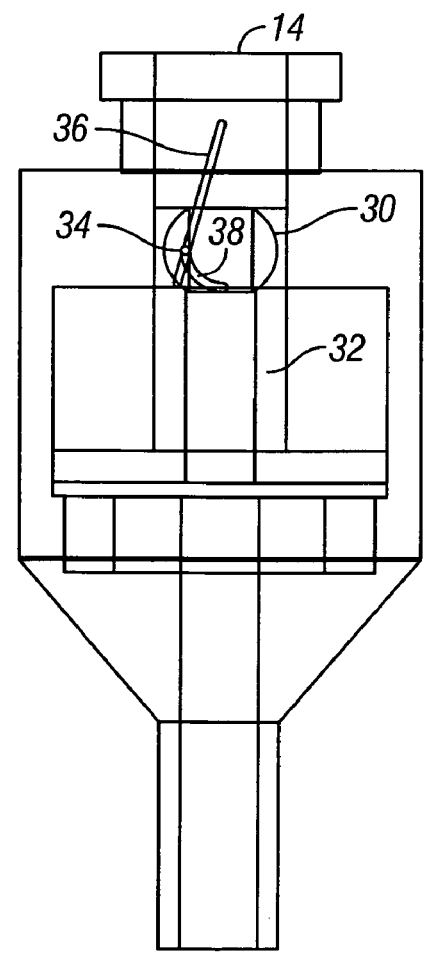

The details of ball valve connection and rotation are shown in FIGS. 2–4, which show sectional views of the hemostasis valve with the ball valve housing positioned at the roof, the middle and the floor of the cavity of the hemostasis valve. FIG. 2 is the same as FIG. 1A in which the hemostasis valve 10 is in a closed position with the opening through the ball valve 30 being at about 90 degrees to the flow path through the hemostasis valve (for the purposes of explanation, the biasing element such as the spring on which the ball valve housing is seated, and the luer fitting have been omitted). FIG. 3 shows the ball valve housing 32 depressed to the middle of the cavity of the hemostasis valve 10. As the ball valve housing 32 is depressed, the guide pin 34 slides down the guide slot 36. The guide pin 34 is located in an arc-shaped slot 38 within the ball valve housing 32. As the guide pin 34 slides down the guide slot 36 within the hemostasis valve housing 12, the movement of the guide pin 34 along the arc-shaped guide slot 38 within the ball valve housing 32 forces the ball valve 30 to rotate in order for the guide pin 34, which is positioned through the ball valve 30, to remain within both the guide slot 36 and the arc-shaped slot 38. FIG. 4 shows the ball valve housing 32 seated near the floor of the cavity of the hemostasis valve 10. In this position, the guide pin 34 is near the bottom of the guide slot 36 in the body of the hemostasis valve 10 and the ball valve 30 is about 90 degrees rotated from the closed position of FIG. 2, resulting in unobstructed flow through the hemostasis valve opening 14.

FIG. 5A shows the details of the ball valve 30. In particular, FIG. 5A illustrates a top view of the ball valve 30 and the ball valve housing 32 with the guide pin 34 located in the ball valve 30 at a position through a mid-portion of the ball valve 30 offset from the opening through the ball valve 30. In FIG. 5A, the ball valve 30 is in an open position resulting in an unobstructed flow through the hemostasis valve 10. The guide pin 34 is located within the ball valve housing 32 in an arc shaped slot as shown in FIGS. 2–4. FIG. 5B illustrates a cross-sectional view taken along line 5B—5B in FIG. 5A, showing a proximal portion of the ball valve housing in which the ball valve is seated (the lower portion of the ball valve housing shown in FIGS. 2–4 is omitted).

As mentioned above, the hemostasis valve of the present invention could be utilized with catheters such as dialysis catheters and power PICCs, which have respective upper limit fluid flow requirements of approximately 8.5 cc/sec and 5.0 cc/sec. The hemostasis valve could provide multiple connector accesses over an extended period of time. One embodiment of the hemostasis valve with such performance characteristics is shown in FIGS. 6A–6C. Hemostasis valve 50 incorporates a plug valve 60, having a sliding cylinder that is angled at the bottom and shaped in the two halves as shown in FIG. 6A. The plug valve 60 is biased in a closed position by a biasing element 56, which in one embodiment is a spring. As the plug valve is pushed downward as shown in FIG. 6B, the angled lower halves of the plug valve 60 engage in the cone shaped base 52 of the cavity 54 of the hemostasis valve 50 and cause the top halves to pivot open on a pivot ball hinge 62 holding the two halves together as shown in FIG. 6C. This opening of the two halves of the plug valve 60 allows fluid flow access from a luer fitting 22 through the hemostasis valve cavity 54 and out through the exit end of the hemostasis valve 50. In one variation, an elastomeric ring such as an O-ring could be wrapped around the two halves of the plug valve within a groove encircling the two halves of the plug valve. The elastomeric ring could serve the function of creating a seal between the plug valve and the inside of the inlet of the hemostasis valve and also force the two halves to automatically retract into a shape of a plug as the luer fitting at the inlet is withdrawn from the inlet.

The hemostasis valve may be designed to be small enough to fit within a cylindrical housing with maximum dimensions of 0.5" diameter and 1.0" length. The hemostasis valve housing and other elements of the hemostasis valve including the ball valve could be made of a metal or a plastic, preferably of a molded plastic. The guide pin is preferably made of a metal. In one embodiment, there could be an O-ring within the hemostasis valve such made of a material such as silicone of 50–60 Shore A and designed to allow the passage of and seal around a guidewire or tube 0.030" to 0.060" diameter when such a guidewire or tube is introduced through the hemostasis valve in the full open position.

The hemostasis valve may also be designed to be incorporated within a small housing that is compatible with multiple fittings, i.e., luer lock, slip fit, compression, etc. Valve function or performance is not affected by the addition of color or clear housing/components. Component or housing components are not affected by opacity or color. Markings and scales could be used on an as needed basis per application. Device function is not integrally linked to markings, etc. Device is sterilizable using standard techniques (EtO, gamma, etc.). The methods of manufacturing the hemostasis valve of the different embodiments include machining or molding the components of the hemostasis valve. While the device is primarily contemplated for use in human patients, the invention will also have veterinary uses or product development purposes in equine, bovine, canine, feline, and other mammalian species.

The present invention has been described above in terms of certain preferred embodiments so that an understanding of the present invention can be conveyed. However, there are many alternative arrangements not specifically described herein, but with which the present invention is applicable. Although specific features have been provided, the present invention would equally be embodied by other configurations not specifically recited herein. The scope of the present invention should therefore not be limited by the embodiments illustrated, but rather it should be understood that the present invention has wide applicability with respect to valve systems generally. All modifications, variations, or equivalent elements and implementations that are within the scope of the appended claims should therefore be considered within the scope of the invention.

What is claimed as new and desired to be protected by Letters Patent of the United States is:

1. A hemostasis valve, comprising:
    a hemostasis valve housing including an inlet, an outlet and a cavity therebetween, the inlet configured to receive a luer fitting;
    a plug valve including two connected halves, each of the connected halves including an angled bottom portion, and a pivot ball hinge connecting the two connected halves to permit the connected halves to pivot open; and
    a biasing element supporting the plug valve, biasing the hemostasis valve in a closed position, the angled bottom portion of each of the connected halves configured to engage a base of the hemostasis valve housing cavity to open the hemostasis valve for fluid flow therethrough.

2. A hemostasis valve, comprising:
    a hemostasis valve housing including an inlet, an outlet, a cavity therebetween and a first guide slot the inlet configured to receive a luer fitting;
    a ball valve housing;
    a ball valve including a second guide slot, the ball valve positioned in the ball valve housing to rotate with respect to the ball valve housing when the ball valve housing is depressed within the hemostasis valve housing;
    a guide pin positioned in the first and second guide slots and connected to the ball valve, the guide pin sliding within the first and second guide slots when the ball valve housing is depressed within the hemostasis valve housing; and
    a biasing element supporting the ball valve housing, biasing the hemostasis valve in a closed position, the hemostasis valve configured to open to permit substantially unobstructed fluid flow therethrough when accessed by a luer fitting.

3. A hemostasis valve comprising:
    a hemostasis valve housing including an inlet configured to receive a luer fitting;
    a ball valve housing positioned and movable within the hemostasis valve housing,
    a ball valve positioned in a proximal portion of the ball valve housing and being rotatable with respect to the ball valve housing, wherein the ball valve includes a guide pin, the guide pin being positioned within both a first and second guide slot, wherein movement of the ball valve housing from a first position to a second position results in movement of the guide pin within the first and second guide slots.

4. The hemostasis valve according to claim 3, wherein the first guide slot is built into the hemostasis valve housing.

5. The hemostasis valve according to claim 3, wherein the first guide slot is linear and is positioned at an angle with respect to a flow path through the hemostasis valve.

6. The hemostasis valve according to claim 3, wherein the second guide slot is built into the ball valve and is arc-shaped, wherein movement of the guide pin within the second guide slot while simultaneously moving within the first guide slot causes rotation of the ball valve.

7. The hemostasis valve according to claim 3, wherein the ball valve includes an opening therethrough.

8. The hemostasis valve according to claim 7, wherein the hemostasis valve is closed to fluid flow in the first position and open to fluid flow in the second position.

9. The hemostasis valve according to claim 8, wherein the ball valve opening is positioned about 90 degrees with respect to the inlet in the first position.

10. The hemostasis valve according to claim 8, wherein the ball valve opening is aligned with a flow path through the hemostasis valve in the second position.

11. The hemostasis valve according to claim 3, further comprising a biasing element supporting the ball valve housing to bias the ball valve housing in the first position.

* * * * *